United States Patent
Heckeroth et al.

(10) Patent No.: US 11,304,934 B2
(45) Date of Patent: *Apr. 19, 2022

(54) USE OF ISOXAZOLINE DERIVATIVES FOR THE TREATMENT OR PREVENTION OF ARTHROPOD INFESTATIONS IN POULTRY

(71) Applicant: Intervet Inc., Madison, NJ (US)

(72) Inventors: Anja Regina Heckeroth, Stadecken-Elsheim (DE); Hartmut Zoller, Hochheim (DE); Annie Flochlay-Sigognault, Angers (FR); Bruno Huyghe, St Martin du Fouilloux (FR)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/849,487

(22) Filed: Apr. 15, 2020

(65) Prior Publication Data

US 2020/0237727 A1   Jul. 30, 2020

Related U.S. Application Data

(63) Continuation of application No. 16/293,024, filed on Mar. 5, 2019, now Pat. No. 10,653,675, which is a continuation of application No. 15/105,197, filed as application No. PCT/EP2014/078636 on Dec. 19, 2014, now Pat. No. 10,272,071.

(30) Foreign Application Priority Data

Dec. 20, 2013   (EP) .................. EP13199007

(51) Int. Cl.
| | |
|---|---|
| *A61K 31/42* | (2006.01) |
| *A61K 31/422* | (2006.01) |
| *A61K 31/437* | (2006.01) |
| *A61K 9/00* | (2006.01) |
| *A61K 47/10* | (2017.01) |
| *A61K 47/26* | (2006.01) |
| *A61K 9/08* | (2006.01) |
| *A01N 43/80* | (2006.01) |
| *A01N 43/90* | (2006.01) |

(52) U.S. Cl.
CPC .............. *A61K 31/42* (2013.01); *A01N 43/80* (2013.01); *A01N 43/90* (2013.01); *A61K 9/0053* (2013.01); *A61K 9/08* (2013.01); *A61K 31/422* (2013.01); *A61K 31/437* (2013.01); *A61K 47/10* (2013.01); *A61K 47/26* (2013.01)

(58) Field of Classification Search
CPC ........ A61K 47/10; A61K 31/42; A01N 25/02; A01N 43/80
See application file for complete search history.

(56) References Cited

U.S. PATENT DOCUMENTS

| | | | |
|---|---|---|---|
| 7,662,972 B2 | 2/2010 | Mita et al. | |
| 10,653,675 B2* | 5/2020 | Heckeroth | ........... A61K 31/422 |
| 2007/0066617 A1 | 3/2007 | Mita et al. | |
| 2010/0125097 A1 | 5/2010 | Soll et al. | |
| 2011/0144349 A1 | 6/2011 | Kousaka et al. | |
| 2013/0065846 A1 | 3/2013 | Soll et al. | |
| 2013/0274302 A1 | 10/2013 | Fuchs et al. | |

FOREIGN PATENT DOCUMENTS

| | | |
|---|---|---|
| CN | 101778566 A | 7/2010 |
| CN | 103260620 A | 8/2013 |
| EP | 1731512 A1 | 12/2006 |
| EP | 2308857 A1 | 4/2011 |
| EP | 2545777 A1 | 4/2014 |
| WO | 2005085216 A1 | 9/2005 |
| WO | 2007053902 A1 | 5/2007 |
| WO | 2007075459 A2 | 7/2007 |
| WO | 2007079162 A1 | 7/2007 |
| WO | 2009002809 A2 | 12/2008 |
| WO | 2009003075 A1 | 12/2008 |
| WO | 2009024541 A2 | 2/2009 |
| WO | 2009080250 A2 | 7/2009 |
| WO | 2010005048 A1 | 1/2010 |
| WO | 2010070068 A2 | 6/2010 |
| WO | 2010079077 A1 | 7/2010 |

(Continued)

OTHER PUBLICATIONS

U.S. Appl. No. 15/105,197, filed Jun. 16, 2016.

(Continued)

*Primary Examiner* — San Ming R Hui
(74) *Attorney, Agent, or Firm* — David J. Kerwick

(57) ABSTRACT

The present invention relates to methods of treating or preventing arthropod infestations of poultry animals and methods of controlling arthropod infestations in poultry animal's environment by administering an isoxazoline compound of formula (I) via drinking water.

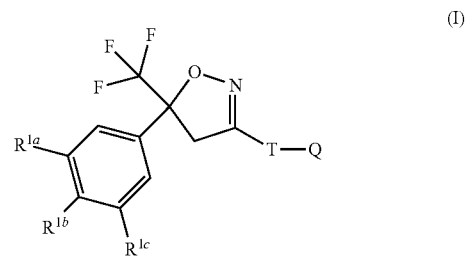

(I)

11 Claims, No Drawings

(56) References Cited

FOREIGN PATENT DOCUMENTS

| WO | 2011154434 A2 | 12/2011 |
|---|---|---|
| WO | 2012089622 A2 | 7/2012 |
| WO | 2012107533 A1 | 8/2012 |
| WO | 2013026695 A1 | 2/2013 |
| WO | 2013026931 A1 | 2/2013 |
| WO | 2013050302 A1 | 4/2013 |
| WO | 2013150055 A1 | 10/2013 |

OTHER PUBLICATIONS

U.S. Appl. No. 16/293,024, filed Mar. 5, 2019.
Qiang, Liu et al (Edited By), Development of New Products of Traditional Chinese Medicines, China Pharmaceutical Science and Technology Press, 2013, 398, 1st Edition.
Qiang, Liu et al (Edited By), Development of New Products of Traditional Chinese Medicines, Products of Traditional Chinese Medicines, 2013, 398, 1st Edition.
Mook, Deborah M. et al., Use of Selamectin and Moxidectin in the Treatment of Mouse Fur Mites, Journal of the American Association for Laboratory Animal Science, 2008, 20-24, 47(3).
Schnabl, B. et al., Oral selamectin in the treatment of canine generalised demodicosis. Veterinary Record, 2010, 710-714, 166.
Hainzl, D. et al., Mechanisms for Selective Toxicity of Fipronil Insecticide and Its Sulfone Metabolite and Desulfinyl Photoproduct, Chem. Res. Toxicol., 1998, pp. 1529-1535, vol. 11.
Hinkle, NC et al., Efficacy and safety assessment of a water-soluble formulation of fluralaner for treatment of natural ornithonyssus sylviarum infestations in laying hens, Parasites & Vectors, 2018, pp. 1-6, 11(99).
International Search Report for PCTEP2014078636 dated Jan. 29, 2015, 9 sheets.
Ozoe, et al., The antiparasitic isoxazoline A1443 is a potent blocker of insect ligand-gated chloride channels, Biochemical and Biophysical Research Communications, 2010, pp. 744-749, vol. 391.
Sparagano OAE et al., Significance and control of the poultry red mite, *Dermanyssus gallinae*, Annu. Rev. Entomol, 2014, pp. 447-466, 59.
Thomas E et al., Field efficacy and safety of fluralaner solution for administration in drinking water for the treatment of poultry red mite (*Dermanyssus gallinae*) intestations in commercial flocks in Europe, Parasites & Vectors, 2017, pp. 1-9, 10(457).

\* cited by examiner

USE OF ISOXAZOLINE DERIVATIVES FOR THE TREATMENT OR PREVENTION OF ARTHROPOD INFESTATIONS IN POULTRY

CROSS-REFERENCE TO RELATED APPLICATIONS

This application is a Continuation of U.S. patent application Ser. No. 16/293,024 filed on Mar. 5, 2019, which is a Continuation of U.S. patent application Ser. No. 15/105,197 filed on Jun. 16, 2016, now U.S. Pat. No. 10,272,071, granted on Apr. 30, 2019; which is a national stage entry under 35 U.S.C. § 371 of PCT/EP2014/078636, filed on Dec. 19, 2014, which claims priority under 35 U.S.C. § 119(e) to application EP Application No. 13199007.9, filed on Dec. 20, 2013, the contents of which are hereby incorporated by reference in their entireties.

FIELD OF INVENTION

The present invention relates to the prevention or treatment of parasitic arthropod infestations of poultry animals and in their environment.

BACKGROUND OF INVENTION

A number of parasitic arthropods infest poultry animals and damage and annoy the animals and therefore present significant challenges in view of economic loss, animal welfare issues and epidemiological concerns for disease transmission.

Poultry mites, such as *Dermanyssus gallinae* (poultry red mite), *Ornithonyssus sylviarum* (northern fowl mite), and *Ornithonyssus bursa* (tropical fowl mite) are important parasite problems, especially in production premises for layers.

Conventional methods of parasitic arthropod control, and especially poultry mite control, include chemicals that are applied as sprays, coarse or solid stream, mist, fog, dusts and/or as wash solutions to empty or populated animal premises and their environment. Other control measures include dusting or spraying the infested poultry animals with powdered or liquid synthetic organic chemicals formulations or adding the powdered synthetic organic chemicals to the litter or dust bath. Examples of synthetic organic chemical groups that have been used in such chemical treatment include pyrethroids, organophosphates, carbamates, spinosad, and the like.

Recently chemical treatments are being increasingly scrutinized due to widespread resistance development, as well as environmental and occupational safety concerns.

Alternatively, amorphous silica is used as an inert dust that kills parasitic arthropods by desiccation. The silica powder treatment can be done in the presence of the poultry animals, but requires a very strong dosage and one is obliged to saturate the silica powder throughout the poultry houses. Moreover, silica powder is known to cause a number of lung diseases both in birds and in human.

An additional problem is that some parasitic arthropods, such as poultry mites, are known to inhabit in cracks and crevices of the poultry houses and hence are difficult to kill using known chemical treatments and silica powder treatment on premises.

Alternative methods including insect attractants/repellents, predatory mites and vaccines have been described, but so far offer no consistent or practical solutions for widespread implementation in poultry operations.

Mite problems often reoccur in affected poultry premises after treatment. Hence, because of the limited efficacy frequent re-treatment is required. Repeated treatments can be stressful for the poultry animals and may especially result in egg production losses in laying hens and breeders.

Therefore, none of these methods satisfies the needs of the poultry producer.

Thus, there is a need in this art to find a better solution to the problem of controlling parasitic arthropods and especially poultry mites in the poultry industry, while not harming animals or humans.

SUMMARY OF THE INVENTION

The current invention provides to use an isoxazoline compound of formula (I)

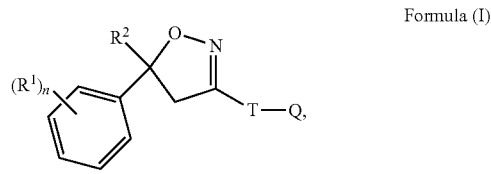

Formula (I)

wherein
$R^1$=halogen, $CF_3$, $OCF_3$, CN,
n=integer from 0 to 3, preferably 1, 2 or 3,
$R^2$=$C_1$-$C_3$-haloalkyl, preferably $CF_3$ or $CF_2Cl$,
T=5- or 6-membered ring, which is optionally substituted by one or more radicals Y,
Y=methyl, halomethyl, halogen, CN, $NO_2$, $NH_2$—C=S, or two adjacent radicals Y form together a chain, especially a three or four membered chain;
Q=X—$NR^3R^4$ or a 5-membered N-heteroaryl ring, which is optionally substituted by one or more radicals;
X=$CH_2$, $CH(CH_3)$, CH(CN), CO, CS,
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

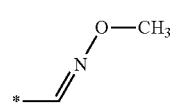

$R^3$-1

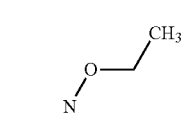

$R^3$-2

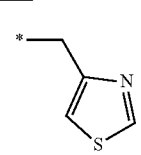

$R^3$-3

R³-4 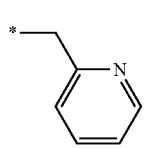

R³-5 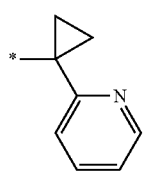

R³-6 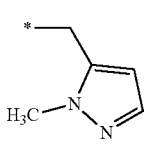

R³-7 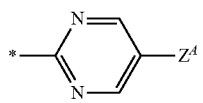

R³-8 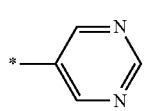

R³-9 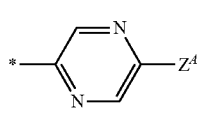

R³-10 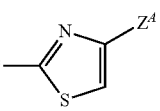

R³-11 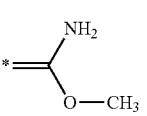

R³-12 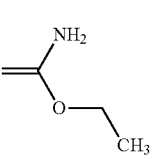

R³-13 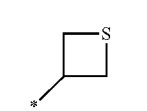

R³-14 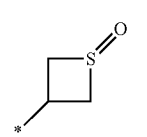

R³-15 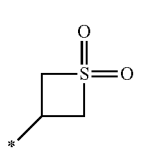

wherein $Z^A$=hydrogen, halogen, cyano, halomethyl ($CF_3$);

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

Or $R^3$ and $R^4$ together form a substituent selected from the group consisting of:

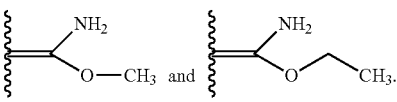

or a salt or solvate thereof in the prevention or treatment of parasitic arthropod infestations of—poultry animals, wherein an effective amount of the isoxazoline compound is administered via the drinking water.

This invention also is directed to a pharmaceutical composition for use in the prevention or treatment of parasitic arthropod infestations of poultry animals, especially fowl animals, especially laying hens via drinking water administration comprising an effective amount of an isoxazoline compound as described in this specification, and a pharmaceutically acceptable carrier.

The current invention further provides a method of controlling arthropods in the environment of poultry animals wherein an isoxazoline compound as described in this specification is administered via drinking water administration to the poultry animals occupying this environment.

DETAILED DESCRIPTION OF THE INVENTION

The inventors of the current invention discovered that parasitic arthropod infestations of poultry animals, especially laying hens can be treated or prevented by administering an effective amount of an isoxazoline compound of formula (I) via the drinking water.

The benefits of such method are that:
a) such method is effective in both treating existing parasitic arthropod infestations and preventing new parasitic arthropod infestation of animals and controlling the parasitic arthropod population in the environment, and hence prevent re-infestation of the animals;
b) the resistance breaking properties of such isoxazoline compounds are very favorable i.e. the parasitic arthropods are very susceptible to the inhibiting or killing effect of such isoxazolines
c) such method is more convenient than prior art application of other compounds in premises, because such method can be used while the poultry animals occupy the premises e.g. in case of laying hens during the laying period, and such method does not require specific safety equipment for the administration (as e.g. required for premise application of synthetic organic chemicals in poultry houses);
d) such method is more convenient than prior art application on animals (e.g. spray application or dust) because it avoids labor intensive techniques and avoids stress in the poultry animals during such prior art methods. Furthermore the spray or dust application of acaricids raises concerns in connection to animal safety and user safety during its administration;

e) such method is easy to apply using available water medication equipment on the poultry farms and therefore requires no or only minimal investments in new equipment; and f) by this method simultaneous administration to a high number of animals during a defined time period is possible and therefore an effective control of the parasitic arthropod population in a whole production unit.

A further advantage of the administration of an isoxazoline compound via drinking water to laying hens is that this allows adjusting the dosage and the administration scheme, so that while still being effective, no discarding of eggs would be necessary because of the very low concentration of the isoxazoline compound, especially fluralaner in the eggs. This uncritical low concentration of fluralaner in eggs allows using eggs for human consumption from laying hens that have been treated with isoxazoline compounds (especially fluralaner).

Consequently, the possibility to administer isoxazoline compounds offers a number of benefits compared to the existing methods of controlling parasitic arthropods in poultry and poultry houses.

The administration of an effective amount of an isoxazoline compound via the drinking water increases egg production, and improves egg size and egg quality compared to infected, but not treated animals. It can further improve reproduction performance in breeding stocks.

As it has been shown in the examples, the administration of isoxazoline compounds of formula (I) as described below, especially fluralaner, by drinking water to poultry animals such as laying hens can effectively control parasitic arthropod infestations of such animals, especially infestations by the red poultry mite and northern fowl mite.

The isoxazoline compound for use in the current invention can be described by Formula (I):

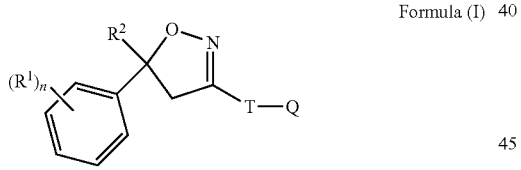

Formula (I)

wherein
$R^1$=halogen, $CF_3$, $OCF_3$, CN,
n=integer from 0 to 3, preferably 1, 2 or 3,
$R^2$=$C_1$-$C_3$-haloalkyl, preferably $CF_3$ or $CF_2Cl$,
T=5- or 6-membered ring, which is optionally substituted by one or more radicals Y,
Y=methyl, halomethyl, halogen, CN, $NO_2$, $NH_2$—C=S, or two adjacent radicals Y form together a chain CH—CH=CH—CH, N—CH=CH—CH, CH—N=CH—CH, CH—CH=N—CH, or CH—CH=CH—N, HC=HC—CH, CH—CH=CH, CH=CH—N, N—CH=CH;
Q=X—$NR^3R^4$ or a 5-membered N-heteroaryl ring, which is optionally substituted by one or more radicals $Z^A$, $Z^BZ^D$;
X=$CH_2$, $CH(CH_3)$, CH(CN), CO, CS,
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

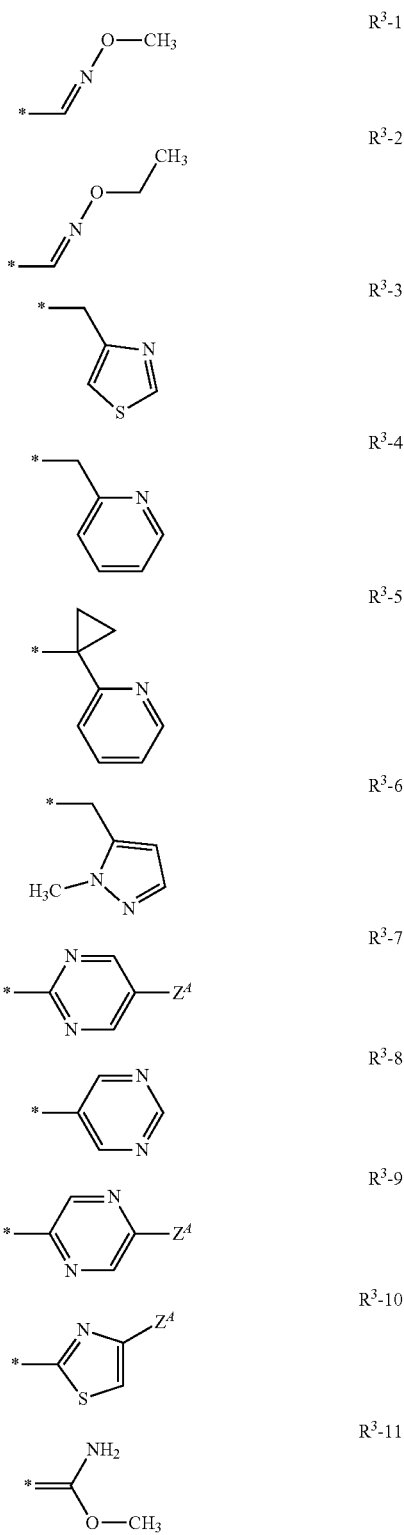

-continued

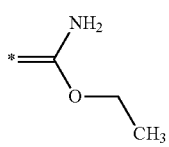
R³-12

R³-13

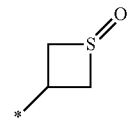
R³-14

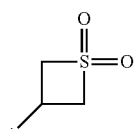
R³-15

R⁴=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl; or R³ and R⁴ together form a substituent selected from the group consisting of:

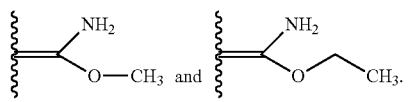

wherein $Z^A$=hydrogen, halogen, cyano, halomethyl ($CF_3$).

In one preferred embodiment in Formula (I) T is selected from

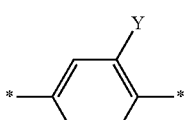
T-1

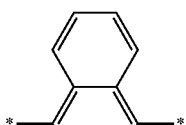
T-2

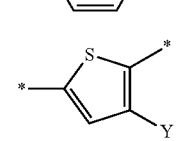
T-3

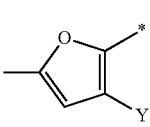
T-4

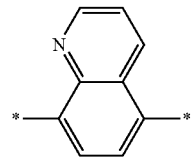
T-5

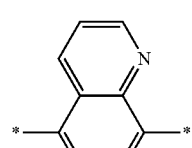
T-6

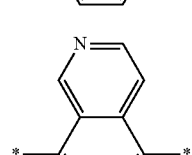
T-7

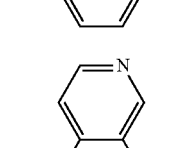
T-8

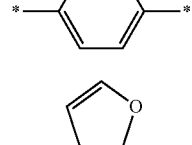
T-9

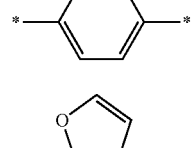
T-10

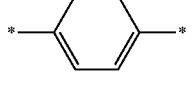
T-11

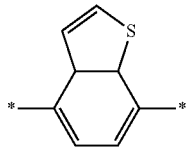
T-12

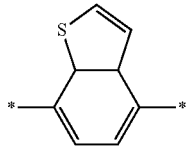
T-13

| | |
|---|---|
| 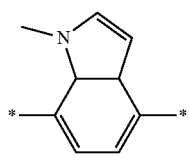 | T-14 |
| 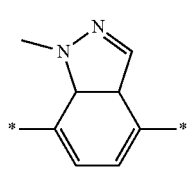 | T-15 |
| 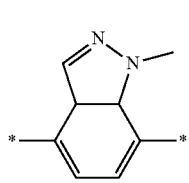 | T-16 |
| 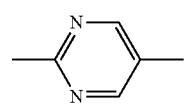 | T-17 |
| 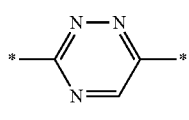 | T-18 |
| 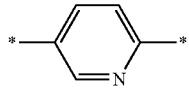 | T-19 |
| 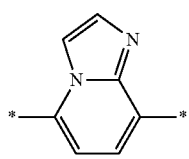 | T-20 |
| 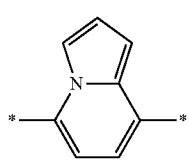 | T-21 |
| 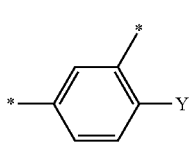 | T-22 |
wherein in T-1, T-3 and T-4 the radical Y is hydrogen, halogen, methyl, halomethyl, ethyl, haloethyl.
In an preferred embodiment in Formula (I) Q is selected from
| | |
|---|---|
| 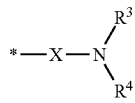 | Q-1 |
| 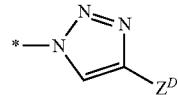 | Q-2 |
|  | Q-3 |
|  | Q-4 |
| 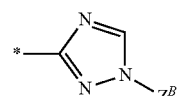 | Q-5 |
| 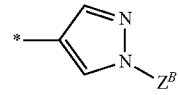 | Q-6 |
| 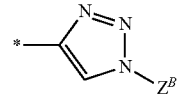 | Q-7 |
| 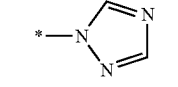 | Q-8 |
| 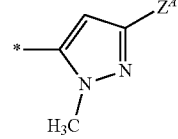 | Q-9 |
wherein $R^3$, $R^4$, X and $Z^A$ are as defined above.
$Z^B =$
| | |
|---|---|
| 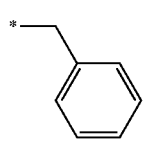 | $Z^B$-1 |
| 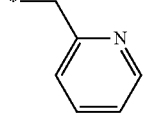 | $Z^B$-2 |
| 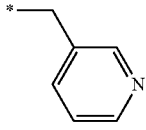 | $Z^B$-3 |

-continued $Z^B$-4

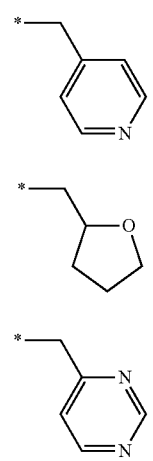

$Z^B$-5

$Z^B$-6

$Z^B$-7

$Z^B$-8

$Z^B$-9

$Z^D =$

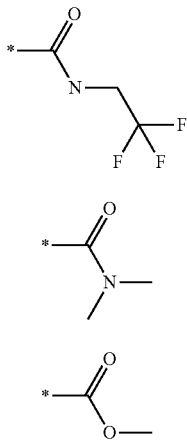

$Z^D$-1

$Z^D$-2

$Z^D$-3

$Z^D$-4

$Z^D$-5

$Z^D$-6

Preferred isoxazoline compounds of Formula (I) for use in the current invention are:

| $(R^1)_n$ | $R^2$ | $R^3$ | $R^4$ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2CH_3$ | H | T-2 | — | Q-1 | — | C(O) |
| 3-Cl, 5Cl | $CF_3$ | $CH_2CH_2OCH_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-Cl, 5Cl | $CF_3$ | $CH_2C(O)NHCH_2CH_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CH_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CH_3$ | H | T-2 | — | Q-1 | — | C(O) |
| 3-Cl, 5Cl | $CF_3$ | — | — | T-2 | — | Q-6 | $Z^B$-7 | |
| 3-Cl, 5Cl | $CF_3$ | — | — | T-2 | — | Q-7 | $Z^B$-7 | |
| 3-Cl, 5Cl | $CF_3$ | — | — | T-2 | — | Q-5 | $Z^B$-7 | |
| 3-Cl, 5Cl | $CF_3$ | — | — | T-2 | — | Q-2 | $Z^D$-1 | |
| 3-Cl, 5Cl | $CF_3$ | $CH_2C(O)NHCH_2CF_3$ | H | T-3 | $CH_3$ | Q-1 | — | C(O) |
| 3-Cl, 5Cl | $CF_3$ | $CH_2C(O)NHCH_2CC$ | H | T-3 | $CH_3$ | Q-1 | — | C(O) |
| 3-Cl, 5Cl | $CF_3$ | $CH_2C(O)NHCH_2CN$ | H | T-3 | $CH_3$ | Q-1 | — | C(O) |
| 3-Cl, 5Cl | $CF_3$ | $CH_2C(O)NHCH_2CH_3$ | H | T-3 | $CH_3$ | Q-1 | — | C(O) |
| 3-$CF_3$, 5-$CF_3$ | $CF_3$ | $CH_2C(O)NHCH_2CF_3$ | H | T-3 | $CH_3$ | Q-1 | — | C(O) |
| 3-$CF_3$, 5-$CF_3$ | $CF_3$ | $CH_2C(O)NHCH_2CH_3$ | H | T-3 | $CH_3$ | Q-1 | — | C(O) |
| 3-Cl, 4-Cl, 5-Cl | $CF_3$ | $CH_2C(O)NHCH_2CF_3$ | H | T-3 | $CH_3$ | Q-1 | — | C(O) |
| 3-Cl, 4-Cl, 5-Cl | $CF_3$ | $CH_2C(O)NHCH_2CH_3$ | H | T-3 | $CH_3$ | Q-1 | — | C(O) |
| 3-Cl, 4-F, 5-Cl | $CF_3$ | $CH_2C(O)NHCH_2CF_3$ | H | T-3 | $CH_3$ | Q-1 | — | C(O) |
| 3-Cl, 4-F, 5-Cl | $CF_3$ | $CH_2C(O)NHCH_2CH_3$ | H | T-3 | $CH_3$ | Q-1 | — | C(O) |
| 3-Cl, 5-Cl | $CF_3$ | $CH_2C(O)NHCH_2CF_3$ | H | T-20 | — | Q-1 | — | C(O) |
| 3-Cl, 5-Cl | $CF_3$ | $CH_2C(O)NHCH_2CH_3$ | H | T-20 | — | Q-1 | — | C(O) |
| 3-$CF_3$, 5-$CF_3$ | $CF_3$ | $CH_2C(O)NHCH_2CF_3$ | $CH_3$ | T-20 | — | Q-1 | — | C(O) |
| 3-$CF_3$, 5-$CF_3$ | $CF_3$ | $CH_2C(O)NHCH_2CH_3$ | $CH_3$ | T-20 | — | Q-1 | — | C(O) |
| 3-$CF_3$, 5-$CF_3$ | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CH_3$ | H | T-20 | — | Q-1 | — | C(O) |

-continued

| (R¹)ₙ | R² | R³ | R⁴ | T | Y | Q | Z | X |
|---|---|---|---|---|---|---|---|---|
| 3-CF₃, 5-CF₃ | CF₃ | CH₂C(O)NHCH₂CF₃ | H | T-21 | — | Q-1 | — | C(O) |
| 3-CF₃, 5-CF₃ | CF₃ | CH₂C(O)NHCH₂CH₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂C(O)NHCH₂CH₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | CH₂C(O)NHCH₂CH₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

Especially preferred isoxazoline compounds for use in the current invention are

| (R¹)ₙ | R² | R³ | R⁴ | T | Y | Q | Z | X |
|---|---|---|---|---|---|---|---|---|
| 3-Cl, 5Cl | CF₃ | CH₂CF₃ | H | T-2 | — | Q-1 | — | C(O) |
| 3-Cl, 5Cl | CF₃ | CH₂CH₃ | H | T-2 | — | Q-1 | — | C(O) |
| 3-Cl, 5Cl | CF₃ | CH₂CH₂OCH₃ | H | T-2 | — | Q-1 | — | C(O) |
| 3-Cl, 5Cl | CF₃ | CH₂C(O)NHCH₂CF₃ | H | T-2 | — | Q-1 | — | C(O) |
| 3-CF₃, 5-CF₃ | CF₃ | CH₂C(O)NHCH₂CF₃ | H | T-2 | — | Q-1 | — | C(O) |
| 3-CF₃, 5-Cl | CF₃ | CH₂C(O)NHCH₂CF₃ | H | T-2 | — | Q-1 | — | C(O) |
| 3-Cl, 5Cl | CF₃ | — | | T-2 | — | Q-6 | $Z^B$-7 | |
| 3-Cl, 5Cl | CF₃ | — | — | T-2 | — | Q-7 | $Z^B$-7 | |
| 3-Cl, 5Cl | CF₃ | — | — | T-2 | — | Q-5 | $Z^B$-7 | |
| 3-Cl, 5Cl | CF₃ | — | — | T-2 | — | Q-2 | $Z^D$-1 | |
| 3-Cl, 5Cl | CF₃ | CH₂C(O)NHCH₂CF₃ | H | T-3 | CH₃ | Q-1 | — | C(O) |
| 3-Cl, 5Cl | CF₃ | CH₂C(O)NHCH₂CC | H | T-3 | CH₃ | Q-1 | — | C(O) |
| 3-Cl, 5Cl | CF₃ | CH₂C(O)NHCH₂CN | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | CH3 | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH2 |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

A more preferred isoxazoline compound for use in the current invention has the Formula (II),

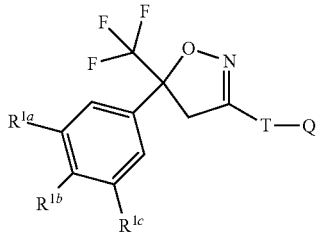

Formula II wherein
$R^{1a}$, $R^{1b}$, $R^{1c}$ are independently from each other hydrogen, Cl or $CF_3$, preferably $R^{1a}$ and $R^{1c}$ are Cl or $CF_3$ and $R^{1b}$ is hydrogen,
T is

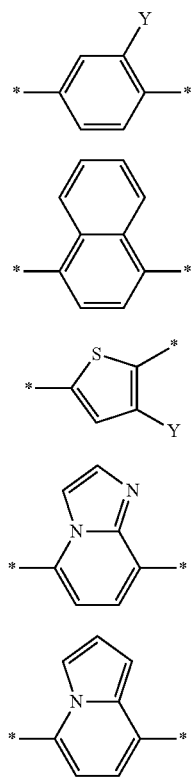

wherein
Y is methyl, bromine, Cl, F, CN or $C(S)NH_2$, and
Q is as described above.

In another preferred embodiment in Formula (II) $R^3$ is H and $R^4$ is —$CH_2$—C(O)—NH—$CH_2$—$CF_3$, —$CH_2$—C(O)—NH—$CH_2$—$CH_3$, —$CH_2$—$CH_2$—$CF_3$ or —$CH_2$—$CF_3$.

In a preferred embodiment the isoxazoline compound is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3-USAN fluralaner).

In another embodiment the isoxazoline compound is (Z)-4-[5-(3,5-Dichlorophenyl)-5-trifluoromethyl-4,5-dihydroisoxazol-3-yl]-N-[(methoxyimino)methyl]-2-methylbenzamide (CAS RN 928789-76-8).

In another embodiment the isoxazoline compound is 4-[5-(3,5-dichlorophenyl)-5-(trifluoromethyl)-4H-isoxazol-3-yl]-2-methyl-N-(thietan-3-yl)benzamide (CAS RN 1164267-94-0) that was disclosed in WO2009/0080250.

In another embodiment the isoxazoline compound is Ethanone, 1-[5'-[(5S)-5-(3,5-dichloro-4-fluorophenyl)-4,5-dihydro-5-(trifluoromethyl)-3-isoxazolyl]spiro[azetidine-3,1'(3'H)-isobenzofuran]-1-yl]-2-(methylsulfonyl)-(Sarolaner) (CAS RN-1398609-39-6).

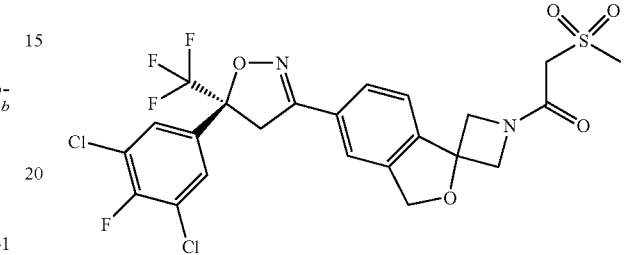

In another embodiment the isoxazoline compound is 2-Thiophenecarboxamide, 5-((5S)-4,5-dihydro-5-(3,4,5-trichlorophenyl)-5-(trifluoromethyl)-3-isoxazolyl)-3-methyl-N-(2-oxo-2-((2,2,2-trifluoroethyl)amino)ethyl)-(INN Lotilaner) (CAS RN-1369852-71-0).

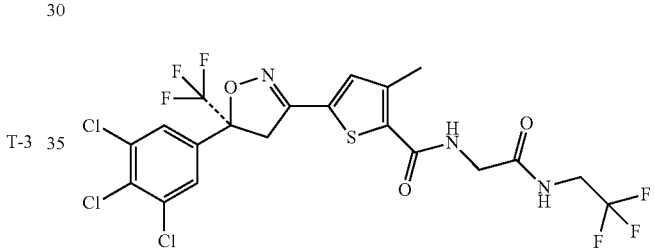

In another preferred embodiment the isoxazoline compound is 4-[5-[3-Chloro-5-(trifluoromethypphenyl]-4,5-dihydro-5-(trifluoromethyl)-3-isoxazolyl]-N-[2-oxo-2-[(2,2,2-trifluoroethyl)amino]ethyl]-1-naphthalenecarboxamide (CAS RN 1093861-60-9, USAN-afoxolaner) that was disclosed in WO2007/079162-.

In another embodiment the isoxazoline compound is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN 1231754-09-8) that was disclosed in WO2010/070068.

Isoxazoline compounds and their use as antiparasitics are e.g. described in US patent application US 2007/0066617, and International Patent applications WO 2005/085216, WO 2007/079162, WO 2009/002809, WO 2009/024541, WO 2009/003075, WO 2010/070068 and WO 2010/079077.

The method (or use) of this invention comprises to use racemic mixtures, for example, equal amounts of the enantiomers of such isoxazoline compounds as described above. In addition, the method of this invention includes isoxazoline compounds that are enriched compared to the racemic mixture in an enantiomer of Formula 1. Also included are the essentially pure enantiomers of such isoxazoline compounds.

When enantiomerically enriched, one enantiomer is present in greater amounts than the other, and the extent of enrichment can be defined by an expression of enantiomeric excess ("ee"), which is defined as (2x-I)-100%, where x is the mole fraction of the dominant enantiomer in the mixture (e.g., an ee of 20% corresponds to a 60:40 ratio of enantiomers). Preferably the compositions for use in the current invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Isoxazoline compounds as described above can comprise additional chiral centers. The method of this invention comprises racemic mixtures as well as enriched and essentially pure stereo configurations at these additional chiral centers.

The reference to isoxazoline compound in this specification includes enantiomers, salts and solvates as well as N-oxides thereof that can be produced by conventional methods.

A number of different parasitic arthropods can lead to infestations of poultry animals, especially laying hens. In case at least one member of parasitic arthropods (an adult parasite or one member of a developmental/larval stage) is continuously or temporary present on the animal, there is an infestation with parasitic arthropods.

Parasitic arthropods are generally ectoparasites that live on or in the skin and feathers of such animals. According to their biological lifecycle they can be separated into stationary or temporary parasitic arthropods.

Stationary parasitic arthropods are those that spend all of their (adult) life on their host, the poultry animal. Examples of important stationary parasitic arthropods of poultry, especially fowl animal are Northern fowl mite (*Ornithonyssus sylviarum*), sticktight flea (*Echidnophaga gallinacean*), hen flea (*Ceratophyllus gallinae*), scaly leg mite (*Knemidokoptes mutans*) and chicken lice, e.g. chicken body louse (*Menacanthus stramineus*) and shaft louse (*Menopon gallinae*).

Temporary parasitic arthropods feed on, but do not permanently live on their host, the poultry animal but spend the majority of their (adult) live in the environment of such host poultry animals. Examples of temporary parasitic arthropods of poultry animals are fowl ticks (*Argas persicus*), poultry red mites (*Dermanyssus gallinae*), tropical fowl mite (*Ornithonyssus bursa*), and bed bugs (*Cimex lectularius*).

The control of temporary parasites is known to be especially difficult because they can be both present on the poultry animal and in the environment.

The inventors of the current invention found that by drinking water administration of one or more of the isoxazoline compounds as defined above to poultry animals both stationary parasitic arthropods and temporary parasitic arthropods of poultry animals can be effectively controlled and both existing infestation of the poultry animals can be treated and re-infestation of the animals from the environment can be prevented.

Furthermore, the drinking water administration of isoxazoline compounds as defined above, especially of fluralaner, effectively reduces the number of parasitic arthropods in the environment of poultry animals.

Furthermore, the drinking water administration of isoxazoline compounds as defined above, especially of fluralaner, in a dosage that is effective to treat or prevent arthropod infestation can be used in laying hens during the egg production period because no discharging of eggs from animals for human consumption would be necessary.

Some important parasitic arthropods that can be combatted by the method and use according to the current invention are described below in more detail:

Mites: Mites are arachnid parasites that infest mammals and poultry animals. Examples of commercially important poultry mites are described below.

The common free-living ectoparasitic mites of poultry belong to the family *Dermanyssidae* and include e.g. the chicken mite, northern fowl mite, and tropical fowl mite. They are bloodsuckers and can run rapidly on skin and feathers.

The poultry red mite (*Dermanyssus gallinae*), also called chicken mite, red mite, or roost mite, is found worldwide and is particularly serious in warmer parts of the temperate zone. The mites stay on the host only to feed, and then move into neighboring cracks and crevices to lay eggs. Under favorable conditions, the life cycle of the parasite can be completed within 1 week and large populations can be rapidly established. These mites may not only produce anemia, thereby seriously lowering production and increasing feed conversion ratio, but actually kill birds, particularly chicks and setting or laying hens. Layers in production may refuse to lay eggs in infested nests. The poultry red mite is a temporary parasitic arthropod.

The mites occur in both battery cages and floor systems. However, the problem is more common and widespread in floor and the "enriched" cage system that has been established in Europe due to animal welfare concerns; due to the presence of numerous suitable hiding places for the mites.

The northern fowl mite (*Ornithonyssus sylviarum*) is the commonest and most important stationary parasite of poultry in all major poultry production areas of the United States. It is also recognized as a serious pest throughout the temperate zone of other countries. These mites suck blood, and the resulting scabs may injure the appearance of dressed poultry. Of greater concern is the economic importance of this mite to egg production from infested caged layers. The northern fowl mite is a stationary parasitic arthropod.

The tropical fowl mite (*Ornithonyssus bursa*) is distributed throughout the warmer regions of the world and possibly replaces the northern fowl mite in these regions. The tropical fowl mite is a temporary parasitic arthropod.

Lice: Lice are common external parasites of birds. They belong in the order *Mallophaga*, the chewing lice. More than 40 species have been reported from domesticated fowl. Many species of bird lice exist, but only a few are commonly seen. Chicken lice are e.g. chicken body louse (*Menacanthus stramineus*) and shaft louse (*Menopon gallinae*). Lice will transfer from one bird species to another if these hosts are in close contact. Lice are not highly pathogenic to mature birds, but louse-infected chicks may die. Clinical evidence indicates that lice may irritate nerve endings, thus, interfering with the rest and sleep. Lousiness frequently accompanies manifestations of poor health such as internal parasitism, infectious disease, and malnutrition, as well as poor sanitation. These are stationary parasitic arthropods.

Bugs: Bugs are another family of parasitic arthropods. The family *Cimicidae* in the order *Hemiptera* includes several bloodsucking parasites of birds. The most widespread of these bugs is the common bedbug (*Cimex lectularius*), which attacks humans, most other mammals, and poultry. It is most prevalent in temperate and subtropical climates. Poultry houses and pigeon lofts may become heavily invaded. The most important bird bug is the poultry bug (*Haematosiphon inodora*). These are temporary parasitic arthropods.

Fleas: Fleas are another family of parasitic arthropods. Fleas (order *Siphonaptera*) are parasites in the adult stage but free-living as larvae. The sticktight flea (*Echidnophaga gallinacea*) occurs more often in the southern United States. Another flea species in chickens is the hen flea (*Ceratophyllus gallinae*). Irritation and blood loss may damage poultry seriously, especially young birds in which death may occur. Production is lowered in older birds. These are stationary parasitic arthropods.

The skilled person will appreciate that the population of parasitic arthropods may be made up of one or more than one species of (parasitic) arthropods. These parasitic arthropods can be temporary or stationary parasite species or it can be a mixed infestation with temporary and stationary parasites (such as e.g. *Dermanyssus gallinae* and *Ornithonyssus sylviarum*).

Infestations of poultry animals, especially fowl animals, especially laying hens with such parasitic arthropod (parasites) can be treated or prevented by administering an effective amount of an isoxazoline compound as described in this application via drinking water administration.

"Poultry animals" are bird animals that are kept for laying eggs or producing meat such as fowl animals, ducks, geese, turkey, pheasants etc. "Fowl animals" are chickens (*Gallus gallus domesticus*).

The term "Laying hen" or "layer" is a common term for adult female chickens (*Gallus domesticus*), that are primarily kept for laying eggs. Such eggs are generally used for consumption as human food. The term "laying hens" in this application includes breeding stocks that are kept for producing eggs from which future laying hens hatch.

"Replacement chickens", also known as grower or pullets, are female chicken animals aged 12-17 weeks. The term "replacement" means that they will be replacing older laying hens destined to be removed at the end of their laying cycle.

"Broilers" are a gallinaceous domesticated fowl, bred and raised specifically for meat production.

By "treating" or "treat" or "treatment" is intended the application or administration of a compound or composition to an animal that has a parasitic infestation for the eradication of the parasite or the reduction of the number of parasites, infesting the animal.

The effect can be e.g. ovicidal, larvicidal and/or adulticidal or a combination thereof. The effect can manifest itself directly, i.e. killing the parasites either immediately or after some time has elapsed, for example when molting occurs, or by destroying their eggs, or indirectly, e.g. reducing the number of eggs laid and/or the hatching rate.

"Prophylaxis" or "prevention" means that a new infestation of the animal with parasites is prevented by killing adult parasites and any development/larval stages, that are able to infest the host, before infestation of the host or, by killing or inhibiting the parasites when they infest an animal that has been treated with an isoxazoline compound as described before or preventing generation of offspring of the parasites e.g. reducing the number of eggs laid and/or the hatching rate.

An "effective amount," is the amount or quantity of an isoxazoline compound as described above that is required to treat or prevent parasitic arthropod infestations of animals, i.e. to alleviate or reduce parasite numbers on an animal, and/or to inhibit the development of parasite infections on an animal, in whole or in part.

This amount is readily determined by observation or detection of the parasite numbers on the animal both before and after administering an isoxazoline compound as described above via drinking water to such animals, e.g. the parasite count is reduced, after a first administration, by 5% to about 100%, preferably more than 50%, more than 70%, more than 90%, more than 95%, more than 99%.

Factors affecting the effective amount may include, for example, the parasite species to be treated and the development stages of the parasites, the type (e.g. species and breed), age, size, sex, diet, activity, and condition of the of the infested animals; the environmental conditions (temperature, humidity), pharmacological considerations, such as the activity, efficacy, pharmacokinetic, and toxicology profiles of the particular isoxazoline compound administered; and whether the isoxazoline compound being administered as part of a combination of active ingredients. Thus, the preferred amount of the compound according to this invention can vary.

It has been found that an effective amount of an isoxazoline compound as described above can be administered to laying hens that is able to combat parasitic arthropods effectively and at the same time no eggs would need to be discarded because of residues.

Such effective amount of an isoxazoline compound, especially fluralaner is in one embodiment split into two dosages that are administered 7 or 14 days apart. Preferably the split dose (each of them containing e.g. 50% of a regular dose) is administered 7 days apart, e.g. 2 times a dose of an isoxazoline compound (e.g. fluralaner) of 0.5 mg/kg bodyweight.

In one embodiment the isoxazoline compound as described above is administered via drinking water administration for treating or preventing mite infestations on fowl animals using a dosage regimen as described in this application. Commercially important mite infestations are infestations by *Dermanyssus* sp. (e.g. *D. gallinae*) and/or *Ornithonyssus* sp. mites. Preferred is the treatment or prevention of infestations with *Dermanyssus gallinae*. Another preferred embodiment is the treatment or prevention of infestations with *Ornithonyssus sylviarum*.

The effective amount of the isoxazoline compound as described above to treat or prevent a parasitic arthropod infestation is generally greater than about 0.01 mg/kg (i.e., milligram of compound according to this invention per kilogram body weight of the treated animals).

In some embodiments, the effective amount is from about 0.01 to about 50 mg/kg, from about 0.05 to about 20 mg/kg, from about 0.1 to 10 mg/kg or from about 0.15 to 5 mg/kg bodyweight, especially 0.2 to 2 mg/kg bodyweight.

In some embodiments the effective amount is from about 0.5 to about 1.5 mg/kg, from about 0.75 to about 1 mg/kg.

In the method according to the current invention the isoxazoline compound is administered via drinking water. For "administration via drinking water" an effective amount of the isoxazoline compound as described above is incorporated in the drinking water that is offered to animals that are either infested by parasitic arthropods (that require treatment) or, to animals, that are not infested, but that are at risk of infestation by parasitic arthropods (prevention of parasitic arthropods). Preferably the isoxazoline compound as defined above is administered to a population that comprises poultry animals that are infested by parasitic arthropods.

By incorporating an effective amount of the isoxazoline compound as described above in the drinking water that is offered to animal, "medicated drinking water" is formed. Such medicated drinking water is administered via the usual drinking water system in the poultry house.

Medicated drinking water is formed by adding to (or mixing with) drinking water a (concentrated) pharmaceutical composition as described below, that is either solved in drinking water, miscible with the drinking water or that result in a suspension of the isoxazoline compound in the drinking water.

The isoxazoline compound in the medicated water needs to be homogeneously distributed during the treatment period (as defined below) and allow the administration of an effective and accurate amount of the compound to all animals that have access to such medicated water. Preferably all animals in a unit, e.g. a poultry house are treated at the same time, i.e. the medicated water is made available to all poultry animals in a certain production unit.

Hence, this invention also is directed to a pharmaceutical composition for use in the prevention or treatment of parasitic arthropod infestations of laying hens that are producing eggs for human consumption, comprising an effective amount of an isoxazoline compound as described above and a pharmaceutically acceptable carrier. Such a pharmaceutical composition is also referred to as "concentrated pharmaceutical composition" or either as "concentrated solution" or "concentrated suspension".

The isoxazoline compound as disclosed above is generally present in such concentrated pharmaceutical compositions in an amount of about 0.1 mg/ml to about 500 mg/ml. A preferred pharmaceutical composition according to the current invention is a concentrated solution. Such concentrated solution comprises between 1.5 mg/ml and 100 mg/ml of the isoxazoline compound, especially fluralaner.

An example for a suitable concentrated solution of isoxazoline compounds, especially fluralaner, is a pharmaceutical composition that comprises an isoxazoline compound, and a pharmaceutically acceptable carrier comprising diethylene glycol monoethyl ether and a polysorbate surfactant.

An alternative concentrated pharmaceutical composition for use in the current invention comprises an isoxazoline compound as described above in the form of a concentrated suspension, especially a concentrated aqueous suspension. Such concentrated suspension comprises between 100 mg/ml and 500 mg/ml of the isoxazoline compound, especially fluralaner.

In one embodiment such concentrated suspension is an aqueous suspension of wet milled isoxazoline compound, especially fluralaner, particles in a composition comprising a polysorbate surfactant. Additionally, such aqueous suspension composition may comprise a preservative such as benzyl alcohol and antifoaming agents such as simethicone.

Such pharmaceutical compositions may be manufactured by processes known in the art. These processes include, for example, a variety of known mixing, dissolving, and emulsifying processes.

For preparation of medicated drinking water in a first step a concentrated pharmaceutical composition, comprising the isoxazoline compound as described above and a pharmaceutically acceptable carrier either as a (micellar) solution, or as a suspension, is prepared. Such concentrated pharmaceutical composition is then diluted (in one or more steps) with water to form medicated drinking water.

Medicated water is produced by diluting an amount (volume) of the (concentrated) pharmaceutical composition that comprises the isoxazoline compound as described above in a dosage that provides (after dilution) an effective amount for all animals treated with a volume of drinking water that corresponds to the volume that will be consumed during the treatment period to a large extent by such animals.

Such medicated drinking water is then offered to the animals for consumption through a drinking water system. Such drinking water systems on commercial farms can be complex systems of tanks, pipes, coils, pen drinkers and cups and/or nipples. An average stable may contain hundreds of meters of pipes with many coils and hundreds of individual cups and/or nipples.

The usual practice is to ensure that medicated drinking water alone is made available to the animals for a limited period of time (treatment period), usually less than 24 hours, e.g. 4-5 hours to 8 hours, as sole drinking water source with the aim of ensuring that an effective amount of the isoxazoline compound as described above is consumed by each animal during this time.

Medicated drinking water can be made available during the treatment period to a single animal; or at the same time to a group of animals or to all animals in a single stable (house) or farm.

The isoxazoline compound as described above can be delivered through a drinking water system of choice by means of mixing and diluting the concentrated pharmaceutical composition as described above with drinking water in the central water tank or separate medication and storage tank to form medicated drinking water that is offered to animals for consumption.

Alternatively, the concentrated pharmaceutical composition as described above is injected continuously into a high or low pressure ring system for drinking water distribution, using a dosage dispenser or dosing pump system or proportioner medication system.

Dosing pump systems rely on a pump that delivers measured amounts of a concentrated composition into the water pipes at a typical dilution of 1-5%. Within the dosing pump systems, electronic dosing pump systems such as KONTI-DOS from Buerkert or mechanical dosing pump such as DOSATRON® water powered dosing pump, DOSMATIC® water-driven, proportional medicators can be used.

The variety of field installations also concerns the water supply systems themselves: dead end or closed loop systems in different lengths with different pipe materials (e.g. PVC, galvanized iron) and the drinkers which are adapted to the target animals such as bell drinkers, nipples.

The isoxazoline compound concentration in the medicated drinking water is depending on the effective amount, the total body weight of the animals treated, the animal water consumption and the treatment period.

The medicator uses for example 10 ml of the concentrated composition and further dilutes with water in about a 1:200 ratio to obtain medicated drinking water having an isoxazoline compound e.g. fluralaner concentration of 0.001 to about 1 mg/ml, especially from about 0.05 to about 0.2 mg/ml. In one embodiment the medicated water has a concentration of between 0.002 and 0.02 mg/ml of the isoxazoline compound.

In one specific embodiment, for the specific isoxazoline compound fluralaner, the concentration is calculated to provide the effective amount of fluralaner per body weight (BW) of the poultry animals being treated in the range of from about 0.5 mg to about 2 mg of fluralaner per kilogram of body weight per day in the volume of drinking water normally consumed by the poultry animals being treated in a 2 to 24 hour treatment period, preferably 4-5 to 8 hours.

A single administration of an effective amount isoxazoline compound as described above can be sufficient to treat a parasitic infestation. However, multiple doses of the isoxazoline compound can be used. One period of making medicated water as described above available to poultry animals (duration generally up to one day) is a single administration visa drinking water.

The treatment frequency of the drinking water administration is depending on the parasite treated or prevented (and its biological lifecycle, which might be dependent on the environmental conditions in the poultry house, e.g. the temperature) and the production cycle of the host poultry animal treated.

Consequently, the isoxazoline compound as described above, especially fluralaner, is administered via drinking water administration at least once or more than once, i.e. 2 times or 3 times in one production cycle of poultry animals. In case of laying hens this is the laying period. In case of other poultry animals a production cycle is the period that a group of poultry animal remains in a poultry house (e.g. the fattening period in case of broilers). Preferred is an administration frequency of two times per laying period. The duration of the laying period varies, but is generally between one year and two years.

Especially preferred are two administrations via the drinking water between 16 and 72 weeks of age of the laying hens.

Preferred is the administration of two doses of isoxazoline compounds as described above approximately 7 days or 14 days apart (depending on the parasite lifecycle and production cycle of the host animal). Especially preferred is the administration of an effective amount of an isoxazoline compound 7 days apart. In a preferred embodiment 1 mg of fluralaner per kg body weight is split in two administrations of 0.5 mg/kg that is administered via drinking water 7 days apart.

By this administration regimen of administration approximately 7 or 14 days apart a longer duration of efficacy against the parasitic arthropods can be achieved, because of the different lifecycle stages of the parasites that can be reached by such administration.

The specific time interval can vary between the various parasitic arthropods and can be depending on the environmental conditions that influence the parasite lifecycle.

With the administration of a second dose the parasites can be reached that developed (following the lifecycle of the parasites) from not susceptible, or difficult to reach parasite stages, e.g. that matured from the juvenile stages of the parasites (such as eggs, nymphs or pupae) during this period.

By such administration regimen the parasite population can be significantly reduced to a level that would only cause minimal damage to the animal and minimal production losses during this production cycle, or even more than one production cycle. One specific benefit of such administration regimen is that a low dosage of the isoxazoline compound can be administered so that residues in eggs can be minimized by such administration regimen while maintaining effective control of parasitic arthropods.

Another aspect of the current invention is a method of controlling harmful arthropods in the environment of poultry animals, especially fowl animals, wherein an isoxazoline compound as described above is administered via the drinking water to the poultry animal(s), especially fowl animals, especially laying hens, occupying this environment.

An poultry animal "occupying this environment" means an animal that is permanently or temporary housed in such environment, has access to such environment either restricted in time (temporarily such as a stable for free ranging hens) or permanently (such as poultry houses for broilers).

An effective amount in the context of this (non-medical) method to control (parasitic) arthropods in the environment of poultry animals is an amount of the isoxazoline compound as described above that is able to reduce arthropod numbers in an animal's environment, e.g. poultry house or stable and/or to inhibit the development of arthropods to a significantly reduced population. Such reduction of the arthropod numbers can be monitored by using special traps in exposed places in the poultry animal's environment.

This amount is readily determined by observation or detection of the parasite numbers in an animal's environment (e.g. by a trap) both before and after administering an isoxazoline compound via drinking water to one or more of the animals occupying such environment, e.g. the arthropod number is reduced by 5% to 100%, especially more than 50%, more than 75%, more than 90%. Preferably the arthropod number in the environment is reduced to a level that does not allow building-up a population during the production cycle that leads to production losses in the poultry animal population occupying such environment (egg production or meat production or animal mortality etc.).

Parasitic arthropods that can be controlled by such method can be both, stages of stationary parasitic arthropods, or stages of temporary parasitic arthropods as described above, that are present in the environment of animals.

The parasitic arthropod stages can be all stages of the lifecycle that are known to the skilled person, i.e. both juvenile developmental/larval stages and adult stages.

In one embodiment the stages of parasitic arthropods as described above that are present in the environment of poultry animals, especially fowl animals, preferably laying hens are controlled.

In one embodiment such arthropods are parasitic arthropods of fowl animals.

The administration of an effective amount of an isoxazoline compound via drinking water administration is useful to control arthropods in the environment of breeding and egg laying poultry animals and other types of fowl that are kept for a production cycle that exceeds a period of approximately 8 weeks, especially if such animals are kept on a commercial scale, such as, laying hens, rearing pullets or replacement chickens, layer breeders, and broiler rearing pullets and breeders.

In general such method can be also used in other types of poultry animals, such as e.g. turkey, geese, ducks, pigeons, quails or pheasants.

In a preferred embodiment such parasitic arthropods are *Dermanyssus* spp. mites and/or *Ornithonyssus* spp. mites, preferably *Dermanyssus gallinae*.

This method is also directed to control arthropods in the environment of poultry animals, especially fowl animal, chickens, and especially laying hens and broiler chickens, that generally do not infest animals directly, but provide harm to the animals.

In one embodiment a method to control darkling beetles is provided by administering an isoxazoline compound as described above to a poultry animal occupying an environment in which darkling beetles are present. The darkling beetle (*Aiphitobius diaperinus*), is the most encountered beetle in the litter of poultry facilities. It is also called darkening or night beetle due to its highest activity at dusk.

Darkling beetles affect birds and poultry producers by reduced performance and production, increased disease potential and transmission and increased building and energy costs due to facility destructions. Darkling beetles are cosmopolitan insects in poultry houses.

The beetles live in the litter, where they feed on spilled poultry feed, manure, and dead or moribund birds. Beetles can be found throughout the poultry house; eggs, larvae, pupae, and adults are in litter and soil. Control is difficult with any single approach, because the beetles use many niches.

In one embodiment arthropods, especially darkling beetles are controlled in the environment of broiler chickens or laying hens. For such control a spray application of an isoxazoline as described above might be used instead of drinking water administration or in addition to drinking water administration.

In such method to control (parasitic) arthropods in the environment of poultry, in general the same isoxazoline compounds, administration regimens, medicated drinking water and pharmaceutical compositions can be used that are described earlier in this specification for the prevention and treatment of parasitic arthropods.

A further aspect of the current invention is a method of controlling temporary parasitic arthropods or arthropods in the environment of poultry animals as defined above comprising the following steps:

1. Evaluating the population of temporary parasitic arthropods (such as e.g. *Dermanyssus gallinae*) in a poultry house by placing traps in places in the poultry animal's environment, that are preferred by such temporary parasites and evaluating the number of parasites caught in such traps.
2. Determining, based on the duration of the production cycle and the number of temporary parasites from the traps and the environmental conditions (e.g. temperature) the "expected parasite pressure" for the poultry animals that occupy such poultry house during the production cycle.
3. Determine the number of treatments per production cycle, necessary to control the parasitic arthropod population to reach a level that does not cause production losses in the poultry animals. The treatments consist of two drinking water administrations of isoxazoline compounds as described above, especially fluralaner, 7 days apart.
4. Measure success of treatment by evaluating the population of arthropods as described in step 1).
5. If the population of arthropods exceeds a certain threshold, adjust treatment schedule.

EXAMPLES

Example 1

The efficacy of fluralaner administered orally via medicated drinking water, to control artificially induced poultry red mite infestations (*Dermanyssus gallinae*) of laying hens was investigated. Groups A-D (n=6) were treated with doses of 2, 1 and 0.5 mg fluralaner/kg BW once or 1 mg fluralaner/kg BW split dose (0.5 mg/kg BW on 2 occasions).

Materials and Methods:

Drinking water consumption in each was measured on three days prior to administration to calculate the average daily water consumption. Medicated water was prepared by diluting a fluralaner solution (10 mg/mL) as shown in the table below to the calculated fluralaner concentration.

| Components | Composition (% w/w) | Composition (mg/mL) | Function |
|---|---|---|---|
| Fluralaner | 0.95% | 10 | Active ingredient |
| Transcutol V (diethylene glycol monoethyl ether) | 24.76% | Up to 1 mL* | Solvent |
| Tween 80 | 74.29% | | Surfactant |

On D0 (group D additionally on D7), the hens in groups A-D received fluralaner via medicated drinking water. Group E received un-medicated drinking water ad libitum.

The dose to be administered was calculated based on average body weights of each treatment group, obtained one day before treatment (D-1, D6). A fluralaner stock solution was diluted in the drinking water to prepare medicated water ready for consumption.

Medicated drinking water was prepared so that fluralaner was administered according to the following dosing regimen:

The volume of medicated water offered per group on D0 (group D also on D7) was approximately 50% of the calculated mean daily water intake measured previously in the respective group in order to ensure consumption of the full dose.

Once all medicated water was consumed the other 50% volume of the mean daily water intake was supplied as tap water in the same drinker.

On Day 1, Day 5, Day 8, Day 12, D15, D19 and D22 four of six hens per group were infested with approximately 200 vital, *D. gallinae* mites (unfed nymphs and adults that starved before infestation for 7 days).

From each infested hen approximately 25 engorged mites were collected and incubated for approximately 24 hours. The dead, damaged and/or live mites were counted visually using a binocular.

Mites were classified as dead if no movement was determined or mites lay in a dorsal position. Mites were classified as damaged if their movement was uncoordinated.

The Mite Mortality and Mite Inhibition percentage was calculated for each treated group in comparison to a not-treated negative control group.

Results:

Fluralaner was well tolerated in hens.

The % Mortality and % Inhibition of red mites (*Dermanyssus gallinae*) assessed approximately 24 hours after the infestation of hens that received fluralaner orally via drinking water are given in Tables 1 and 2. A fast onset of action was demonstrated for all administered doses.

TABLE 1

% Mortality of *D. gallinae* assessed 24 hours after infestation

| Group | fluralaner (mg/kg BW) | % Mortality of mites 24 hours after infestation on | | | | | | |
|---|---|---|---|---|---|---|---|---|
| | | D1 | D5 | D8 | D12 | D15 | D19 | D22 |
| A | 2 | 100 | 100 | 100 | 100 | 77 | 1 | 0 |
| B | 1 | 100 | 100 | 100 | 94 | 77 | 2 | 0 |
| C | 0.5 | 100 | 100 | 97 | 55 | 15 | 0 | 0 |
| D | 1 (2 × 0.5) | 100 | 100 | 100 | 100 | 98 | 59 | 14 |

TABLE 2

| | fluralaner (mg/kg BW) | % Inhibition of mites 24 hours after infestation on | | | | | | |
|---|---|---|---|---|---|---|---|---|
| Group | | D1 | D5 | D8 | D12 | D15 | D19 | D22 |
| A | 2 | 100 | 100 | 100 | 100 | 81 | 14 | 0 |
| B | 1 | 100 | 100 | 100 | 95 | 81 | 3 | 0 |
| C | 0.5 | 100 | 100 | 100 | 75 | 19 | 0 | 0 |
| D | 1 (2 × 0.5) | 100 | 100 | 100 | 100 | 99 | 66 | 27 |

% Inhibition of *D. gallinae* assessed 24 hours after infestation

On each assessment time points, mites observed from the untreated control group were vital and showed their normal behavior.

The invention claimed is:

1. A method of preventing or treating an infestations of a laying hen by a temporary parasitic arthropod comprising administering via the drinking water an effective amount of an isoxazoline compound wherein the isoxazoline compound is sarolaner or a salt or solvate thereof

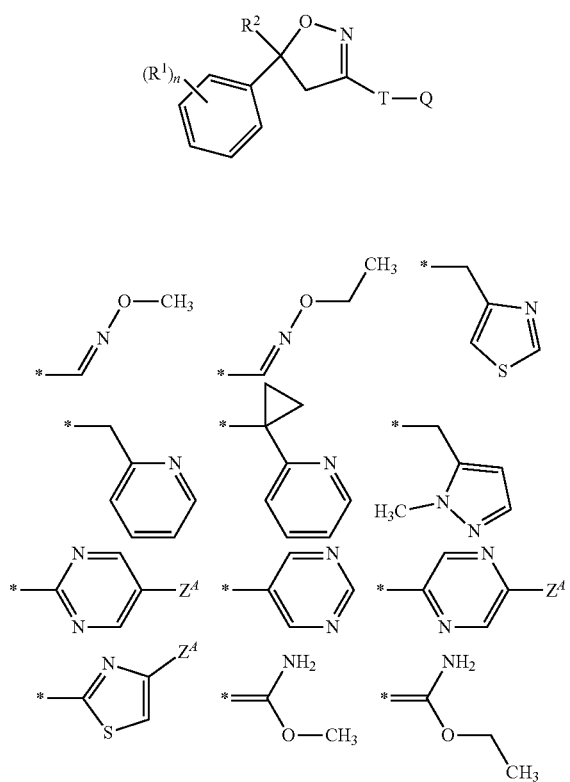

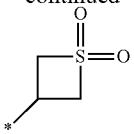

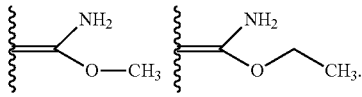

2. The method according to claim 1 wherein the temporary parasitic arthropod is selected from fowl ticks (*Argas persicus*), poultry red mites (*Dermanyssus gallinae*), tropical fowl mite (*Ornithonyssus bursa*) and bed bugs (*Cimex lectularius*).

3. The method according to claim 1 wherein the temporary parasitic arthropod infestation is a mite infestation.

4. The method of claim 1 wherein the temporary parasitic arthropod infestation is an infestation by *Dermanyssus* spp. and/or *Ornithonyssus* spp. mites.

5. The method of claim 1 wherein the temporary parasitic arthropod infestation is an infestation by *Dermanyssus gallinae*.

6. The method according to claim 1 wherein the effective amount is between 0.01 and 50 mg/kg body weight of animals treated.

7. The method according to claim 1 wherein the effective dose of the isoxazoline compound is administered via the drinking water in two separate dosages.

8. The method according to claim 7 wherein the two separate dosages of isoxazoline compound are administered approximately 7 days apart.

9. The method according to claim 7 wherein the two separate dosages of isoxazoline compound are administered approximately 14 days apart.

10. A method for the prevention or treatment of parasitic arthropod infestations of laying hens during the laying period comprising administering via drinking water an effective amount of an isoxazoline compound wherein the isoxazoline compound is sarolaner or a salt or solvate thereof, and a pharmaceutically acceptable carrier.

11. A Method of controlling darkling beetles in the environment of poultry animals comprising administering via drinking water an effective amount of an isoxazoline compound wherein the isoxazoline compound is sarolaner or a salt or solvate thereof.

* * * * *